United States Patent [19]

Corrigan et al.

[11] Patent Number: 5,480,667
[45] Date of Patent: * Jan. 2, 1996

[54] NONDIGESTIBLE FAT COMPOSITIONS CONTAINING DIVERSELY ESTERIFIED POLYOL POLYESTER FOR PASSIVE OIL LOSS CONTROL

[76] Inventors: Patrick J. Corrigan; John K. Howie; Peter Y. T. Lin, all of 6071 Center Hill Ave., Cincinnati, Ohio 45224-1703

[*] Notice: The portion of the term of this patent subsequent to Jun. 6, 2012, has been disclaimed.

[21] Appl. No.: 321,381

[22] Filed: Oct. 11, 1994

Related U.S. Application Data

[63] Continuation of Ser. No. 968,780, Oct. 30, 1992, abandoned.
[51] Int. Cl.⁶ ......................................... A23L 1/00
[52] U.S. Cl. ..................... 426/531; 426/601; 426/611; 426/637; 426/804; 536/119; 554/227
[58] Field of Search .................... 426/438, 531, 426/549, 601, 606, 607, 609, 610, 611, 612, 804, 637; 536/119; 554/161, 227

[56] References Cited

U.S. PATENT DOCUMENTS

| | | | |
|---|---|---|---|
| 2,266,591 | 12/1941 | Eckey et al. | 99/163 |
| 2,962,419 | 11/1960 | Minich | 167/81 |
| 3,059,009 | 10/1962 | Schmid et al. | 260/428 |
| 3,059,010 | 10/1962 | Schmid et al. | 260/428 |
| 3,093,481 | 6/1963 | Eckey et al. | 99/118 |
| 3,158,490 | 11/1964 | Baur et al. | 99/118 |
| 3,353,966 | 11/1967 | Hugenberg et al. | 99/163 |
| 3,353,967 | 11/1967 | Lutton | 99/163 |
| 3,495,010 | 2/1970 | Fossel | 424/312 |
| 3,495,011 | 2/1970 | Fossel | 424/312 |
| 3,600,186 | 8/1971 | Mattson et al. | 99/1 |
| 3,649,647 | 3/1972 | Ota | 260/345.8 |
| 4,005,195 | 1/1977 | Jandacek | 424/180 |
| 4,005,196 | 1/1977 | Jandacek et al. | 424/180 |
| 4,368,213 | 1/1983 | Hollenbach et al. | 426/590 |
| 4,797,300 | 1/1989 | Jandacek et al. | 426/549 |
| 5,017,398 | 5/1991 | Jandacek et al. | 426/603 |
| 5,085,884 | 2/1992 | Young et al. | 426/611 |
| 5,102,683 | 4/1992 | Letton et al. | 426/601 |
| 5,137,743 | 8/1992 | Zaks et al. | 426/602 |
| 5,158,796 | 10/1992 | Bernhardt et al. | 426/549 |
| 5,194,270 | 3/1993 | Cante et al. | 426/74 |
| 5,219,604 | 6/1993 | Klemann et al. | 426/531 |
| 5,225,049 | 7/1993 | Barmentlo et al. | 203/34 |
| 5,230,913 | 7/1993 | Klemann | 426/97 |
| 5,236,733 | 8/1993 | Zimmerman et al. | 426/611 |

FOREIGN PATENT DOCUMENTS

| | | |
|---|---|---|
| 233856 | 8/1987 | European Pat. Off. . |
| 236288 | 9/1987 | European Pat. Off. . |
| 311154 | 4/1989 | European Pat. Off. . |
| 0325463 | 7/1989 | European Pat. Off. ...... C07C 69/675 |
| 390410 | 10/1990 | European Pat. Off. . |
| 424066 | 4/1991 | European Pat. Off. . |
| 434117 | 6/1991 | European Pat. Off. . |
| 434119 | 6/1991 | European Pat. Off. . |
| 227137 | 9/1985 | Germany . |
| 49-26220 | 3/1974 | Japan . |
| 52-27694 | 7/1977 | Japan . |
| 58-78531 | 5/1983 | Japan . |
| 9062511A | 4/1984 | Japan . |
| 59-143550 | 8/1984 | Japan . |
| 59-156242 | 9/1984 | Japan . |
| 2020247A | 1/1990 | Japan . |
| 3-81042 | 8/1992 | Japan ........................ A23D 9/00 |
| 04237458A | 8/1992 | Japan . |
| WO91/15962 | 10/1991 | WIPO . |
| WO91/15963 | 10/1991 | WIPO . |
| WO91/15961 | 10/1991 | WIPO . |
| WO91/15960 | 10/1991 | WIPO . |
| WO92/04360 | 3/1992 | WIPO . |
| 92/03937 | 3/1992 | WIPO ........................ A23L 1/308 |
| 92/17077 | 10/1992 | WIPO ........................ A23L 1/308 |

*Primary Examiner*—Leslie Wong
*Attorney, Agent, or Firm*—Tara M. Rosnell; G. W. Allen; Rose Ann Dabek

[57] ABSTRACT

Nondigestible fat compositions useful as a replacement for triglyceride fats or oils in foods are disclosed. These compositions have relatively flat Solid Fat Content (SFC) profile slopes between typical room and body temperatures. The nondigestible fat compositions comprise a liquid nondigestible oil and nondigestible particles of solid polyol polyester material dispersed in the oil in an amount sufficient to control passive oil loss. The ester groups of the solid polyol polyester material comprise (i) at least about 15% ester groups formed from $C_{20}$–$C_{26}$ long chain saturated fatty acid radicals, and (ii) ester groups formed from fatty or other organic acid radicals which are dissimilar said long chain saturated fatty acid radicals. The molar ratio of said dissimilar acid radicals to said long chain saturated fatty acid radicals ranges from about 0.1:7.9 to about 3:5. Moreover, the dissimilar acid radicals cannot consist solely of $C_2$–$C_{12}$ short chain saturated fatty acid radicals, $C_{20}$ or higher long chain unsaturated fatty acid radicals, or a combination of said short chain saturated and said long chain unsaturated fatty acid radicals. Edible fat-containing products containing these nondigestible fat compositions can be less waxy tasting due to the lower level of solids required for passive oil loss control.

19 Claims, 1 Drawing Sheet

NONDIGESTIBLE FAT COMPOSITIONS CONTAINING DIVERSELY ESTERIFIED POLYOL POLYESTER FOR PASSIVE OIL LOSS CONTROL

This is a continuation of application Ser. No. 07/968,780, filed on Oct. 30, 1992 now abandoned.

TECHNICAL FIELD

The present invention relates to nondigestible fat compositions that are useful as full or partial replacers for triglyceride fats or oils in foods. More particularly, the present invention provides such nondigestible fat compositions that provide passive oil loss control without being excessively waxy tasting.

BACKGROUND OF THE INVENTION

Certain polyol fatty acid polyesters have been suggested as low or reduced calorie substitutes for triglyceride fats and oils used in foods. For example, nonabsorbable, nondigestible sugar fatty acid esters or sugar alcohol fatty acid esters having at least 4 fatty acid ester groups with each fatty acid having from 8 to 22 carbon atoms have been used as partial or full fat replacers in low calorie food compositions. (See Mattson & Volpenhein; U.S. Pat. No. 3,600,186; Issued Aug. 17, 1971.) Foods in which these polyol polyesters are particularly useful as partial or complete replacements for triglyceride fats or oils include products suitable for use in frying. Unfortunately, regular ingestion of moderate to high levels of completely liquid forms of these polyol polyesters can produce undesirable passive oil loss, namely, leakage of the polyesters through the anal sphincter. By contrast, completely sol id versions of these polyesters provide a sufficiently high solids content at mouth temperatures (e.g., 92° F., 33.3° C.) such that they give a waxy taste or impression in the mouth when ingested.

As an alternative to these completely liquid or completely solid nondigestible/nonabsorbable polyol polyesters, certain intermediate melting polyol fatty acid polyesters have been developed that provide passive oil loss control, while at the same time reducing waxiness in the mouth. (See Bernhardt; European Patent Application Nos. 236,288 and 233,856; Published Sep. 9, and Aug. 26, 1987, respectively.) These intermediate melting polyol polyesters exhibit a unique rheology at body temperature by virtue of their having a matrix which involves a minimal level of solids (e.g. about 12% or lower) that bind the remaining liquid portion. As a result, these intermediate melting polyol polyesters are sufficiently viscous and have a sufficiently high liquid/solid stability at body temperature to provide passive oil loss control. An example of such intermediate melting polyol polyesters are those obtained by substantially completely esterifying sucrose with a 55:45 mixture of fully hydrogenated (hardstock) and partially hydrogenated soybean oil fatty acid methyl esters. (See Examples 1 and 2 of the above European patent applications.)

These intermediate melting polyol polyesters can be used as total or partial replacements for other fats and oils in various food products, including cooking and frying oils. However, it has been found that certain foods such as potato chips fried in frying fats containing substantial levels of these nondigestible intermediate melting polyol polyesters, particularly at levels in excess of about 40%, can give a significantly increased waxiness impression compared to potato chips that have been fried in the digestible triglyceride fat or oil that the nondigestible polyol polyester has partially replaced. (In terms of physical properties, "waxiness" relates to how the fat composition is sensed in the mouth, and specifically relates in part to the sensation of the product having a relatively high level of solids.) Indeed, this increased waxiness impression with regard to these intermediate melting polyol polyesters is recognized in the aforementioned European Patent Application No. 233,856 inasmuch as that application discloses fat compositions which contain digestible food materials, such as triglycerides and substituted mono- and diglycerides, that act as solvents for the intermediate melting polyol polyesters. However, as the proportion of triglycerides is increased relative to the intermediate melting polyol polyesters so as to impart less waxiness, the caloric content of the frying fat also increases accordingly. In addition, it has been found that frying fats containing greater than about 40% of these intermediate melting polyol polyesters can adversely affect the flavor display of the resulting fried food, in particular potato chips.

The waxiness impression imparted by intermediate melting polyol polyesters such as those of the aforementioned European '288 and '856 applications is believed to be due at least in part to their change in Solid Fat Content (SFC), particularly between typical room temperature (i.e. 70° F., 21.1° C.) and body temperature (i.e. 98.6°, 37° C.). For example, the intermediate melting sucrose polyester of Example 2 of European Patent Application Nos. 233,856 and 236,128 has an SFC profile slope (as hereinafter defined) between room temperature and body temperature of about −1.3. In other words, the SFC profile slope of these intermediate melting polyol polyesters is relatively steep. Given this relatively steep SFC profile slope, the change in solids content of these intermediate melting polyol polyesters can be sufficiently great such that a high level of solids will be sensed when such room temperature materials are first placed in the mouth, thereby leading to an increased waxiness sensation.

Blends of completely liquid polyol polyesters with completely solid polyol polyester hardstocks, preferably esterified with $C_{10}$–$C_{22}$ saturated fatty acids (e.g. sucrose octastearate), have also been proposed in order to provide passive oil loss control. (See, for example, Jandacek; U.S. Pat. No. 4,005,195; and Jandacek/Mattson; U.S. Pat. No. 4,005,196; Both issued Jan. 25, 1977.) Blends of these liquid polyol polyesters and solid polyol polyesters hardstocks have relatively flat SFC profile slopes between typical room temperature and body temperature, i.e. slopes of from 0 to about −0.3, and more typically from 0 to about −0.1. In other words, there is little or no change in the solids content of these blends between room temperature and body temperature.

Although providing at least temporary passive oil loss control, blends of liquid polyol polyesters and solid polyol polyester hardstocks according to the aforementioned U.S. '195 and '196 patents do not necessarily provide passive oil loss control over an extended period of time. It has been found that these solid polyol polyester hardstocks normally tend to form large spherulitic particles (typically from about 3 to about 32 microns in size) in the liquid polyol polyesters. These large spherulitic particles may tend to phase separate from the liquid polyol polyesters during storage of such blends. As a result, a two-phase system can develop with the liquid portion thereof providing minimal or no passive oil loss control.

In addition, blends of liquid polyol polyesters and solid polyol polyester hardstocks according to the aforementioned U.S. Pat. Nos. 4,005,195 and 4,005,196 do not necessarily lead to less waxy tasting products. As taught in these patents, a relatively high level of solid polyol polyester hardstock is required to provide passive oil loss control. For example, hardstock is preferably used in an amount of from about 20% to about 50% by weight of the liquid polyol polyester. (See Column 9, lines 65–68, of U.S. Pat. No. 4,005,195.) Such a level of solid polyol polyester hardstock used for passive oil loss control at body temperature can lead to a waxy tasting product due to the relatively high level of solids that will also be present at mouth temperature.

In view of the foregoing, it would be desirable to provide nondigestible fat compositions comprising blends of liquid polyol polyesters and solid polyol polyester hardstock particles with such blends exhibiting little or no phase separation of the hardstock particles from the liquid polyol polyesters. In addition, it would be desirable to be able to reduce the level of solid polyol polyester hardstock required for effective passive oil loss control so as to provide less waxy tasting products.

In addition to being useful as passive oil loss control agents when combined with liquid nondigestible oils, certain polyol polyesters which are solid at temperatures of about 25° C. and higher have also been used as thickening agents for conventional digestible triglyceride oils. For example, these solid polyol polyesters have been used as "thickening agents" for blending with liquid digestible or nondigestible oils in formulations such as shortenings, as well as in other food products which contain a combination of fat and non-fat ingredients, e.g., margarines, mayonnaise, frozen dairy desserts and the like. (See, for example, Jandacek and Letton; U.S. Pat. No. 4,797,300; Issued Jan. 10, 1989.) However, these prior art thickening agents had to be used at levels of 10 to 25%. Accordingly, it would be desirable to reduce the level of thickening agents of this type in order to provide less waxy tasting products.

SUMMARY OF THE INVENTION

The present invention relates to nondigestible fat compositions which are useful as replacements for triglyceride fats and oils in food products. Such compositions have a Solid Fat Content (SFC) profile slope between room temperature (70° F.) and body temperature (98.6° F.) of from 0 to about −0.75 % solids/° F. Such compositions further comprise a liquid nondigestible oil having dispersed therein nondigestible solid polyol polyester particles in an amount sufficient to control passive oil loss upon the ingestion of the nondigestible fat compositions.

The liquid nondigestible oil component of the compositions herein is one which has a complete melting point below about 37° C. The polyol polyesters which can be used to form the solid nondigestible particles in the compositions herein are those wherein the ester groups thereof consist essentially of (i) at least about 15% ester groups formed from long chain ($C_{20}$ or higher) saturated fatty acid radicals, and (ii) other ester groups formed from fatty or other organic acid radicals which are dissimilar to said long chain saturated fatty acid radicals. The molar ratio of dissimilar acid radicals to long chain saturated fatty acid radicals ranges from about 0.1:7.9 to about 3:5. Moreover, the dissimilar acid radicals cannot consist solely of short chain ($C_2$–$C_{12}$) saturated fatty acid radicals, long chain ($C_{12}$ or higher) unsaturated fatty acid radicals or a combination of said short chain saturated or long chain unsaturated fatty acid radicals.

The nondigestible fat compositions of the present invention provide significant advantages over known intermediate melting polyol polyesters, as well as prior art blends of liquid polyol polyesters and solid polyol polyester hardstocks. The relatively small nondigestible particles provide especially efficient passive oil loss control. As a result, the level of solids at body temperature required for passive oil loss control can be reduced to relatively low levels, (e.g., to less than about 20%, more preferably, to less than about 15% of the nondigestible fat). In addition, the nondigestible fats of the present invention have relatively flat SFC profile slopes, thus leading to minimal or no change in solids content between typical room and body temperature. This combination of the relatively low solids levels required for passive oil loss control, with minimal or no solids content change between room and body temperatures, can result in less waxy tasting products containing these nondigestible fats.

The present invention also relates to digestible fat compositions which utilize particles of the hereinbefore described nondigestible polyol polyester material as thickening agents. Such compositions comprise from about 85% to about 99% of a digestible edible oil and from about 1% to about 15% of the nondigestible solid polyol polyester particles.

DETAILED DESCRIPTION OF THE INVENTION

A. Definitions

Figure 1:
FIGURE 1 is a photomicrograph (magnification 1000X) depicting particles of diversely esterified solid polyol polyester material containing toluic acid as the dissimilar acid radical, said solid polyol polyester dispersed in a liquid sucrose polyester.

By "nondigestible" is meant that only about 70% or less of the material can be digested by the body. Preferably, only about 20% or less of such materials can be digested, more preferably only 1% or less of such materials can be digested.

As used herein, the term "thickness" of a particle is used in its conventional sense of the smallest of the three dimensions (length, width, height) of any given particle.

As used herein, the term "spherulitic" refers to substantially spherical or round, essentially three-dimensional particles.

As used herein, the term "platelet-like" refers to a substantially flat, essentially two-dimensional type of particle having length and width in the unfolded planar configuration that is substantially greater in dimension than its thickness.

As used herein the terms "filament-like" and "rod-like" refer to elongated, essentially one-dimensional particles.

As used herein, the term "complete melting point" refers to the temperature at which all solid components have melted. All melting points referred to herein are measured by Differential Scanning Calorimetry (DSC) as described hereinafter.

As used herein, the term "comprising" means various components, or steps, can be conjointly employed in the nondigestible fat compositions and processes of the present invention. Accordingly, the term "comprising" encompasses the more restrictive terms "consisting essentially of", "consisting of", and "consisting solely of".

As used herein, the term "not consisting solely of" means consisting of less than 100%, preferably consisting of less than 80%, more preferably consisting of less than 60%.

By "polyol" is meant a polyhydric alcohol containing at least 4, preferably from 4 to 12, more preferably from 4 to 8, most preferably from 6 to 8, hydroxyl groups. Polyols thus include sugars (i.e., monosaccharides, disaccharides and trisaccharides), sugar alcohols (i.e., the reduction product of sugars wherein the aldehyde or ketone group has been reduced to an alcohol), other sugar derivatives (e.g., alkyl glycosides), polyglycerols such as diglycerol and triglycerol, pentaerythritol, and polyvinyl alcohols. Specific examples of suitable sugars, sugar alcohols, and sugar derivatives include xylose, arabinose, ribose, xylitol, erythritol, glucose, methyl glucoside, mannose, galactose, fructose, sorbitol, maltose, lactose, sucrose, raffinose, and maltotriose. Preferred polyols include erythritol, xylitol, sorbitol, and glucose, with sucrose being an especially preferred polyol.

By "polyol polyester" is meant a polyol as hereinbefore defined having at least 4 ester groups, i.e., at least 4 of the hydroxyl groups are esterified with fatty or other organic acids. Polyol esters that contain 3 or less ester groups are digested in (and the products of digestion are absorbed from) the intestinal tract much in the manner of ordinary triglyceride fats or oils, whereas those polyol esters which contain 4 or more ester groups are generally substantially nondigestible and consequently nonabsorbable by the human body. It is not necessary that all of the hydroxyl groups of the polyol be esterified, but it is preferable that disaccharide molecules contain no more than 3 unesterified hydroxyl groups, and more preferably no more than 2 unesterified hydroxyl groups, so that they are rendered nondigestible. Typically, substantially all (e.g., at least about 85%) of the hydroxyl groups of the polyol are esterified. For liquid polyol polyesters, preferably at least about 95% of the hydroxyl groups of the polyol are esterified. In the case of sucrose polyesters, typically from about 7 to 8 of the hydroxyl groups of the polyol are esterified.

By "ester group" is meant a moiety formed from the reaction of a hydroxyl group with an organic acid or acid derivative which moiety contains fatty acid and/or other organic radicals having at least 2 carbon atoms, typically at least 8 carbon atoms, more typically at least 12 carbon atoms, and most typically at least 16 carbon atoms. Representative examples of such fatty and other organic acid radicals include acetic, propionic, butyric, caprylic, capric, lauric, myristic, myristoleic, palmitic palmitoleic, stearic, oleic, elaidic, ricinoleic, linoleic, linolenic, eleostearic, arachidic, arachidonic, behenic, lignoceric, erucic, and cerotic fatty acid radicals and other organic acid radicals including aromatic esters such as benzoic and toluic; branched chain radicals such as isobutyric, neooctanoic or methyl stearic; ultra-long chain saturated or unsaturated fatty acid radicals such as tricosanoic or tricosenoic; cyclic aliphatics such as cyclohexane carboxylic; and polymeric ester-forming radicals such as polyacrylic and dimer fatty acid. The fatty acid or other organic radicals can be derived from naturally occurring or synthetic acids. The acid radicals can be saturated or unsaturated, including positional or geometric isomers, e.g. cis- or trans-isomers, straight or branched chain aliphatic or aromatic, and can be the same for all ester groups, or can be mixtures of different acid radicals.

By "dimer fatty acid radical" is meant dibasic acid such as that produced by dimerization of the fatty acids or fatty acid lower esters of any of a number of polyunsaturated vegetable oils such as soybean oil or cottonseed oil or animal fats such as tallow.

All percentages, ratios and proportions used herein are by weight unless otherwise specified.

B. Liquid Nondigestible Oil

A key component of the nondigestible fat compositions herein is a liquid nondigestible oil having a complete melting point below about 37° C. Suitable liquid nondigestible edible oils for use herein include liquid polyol fatty acid polyesters (see Jandacek; U.S. Pat. No. 4,005,195; Issued Jan. 25, 1977); liquid esters of tricarballylic acids (see Hamm; U.S. Pat. No. 4,508,746; Issued Apr. 2, 1985); liquid diesters of dicarboxylic acids such as derivatives of malonic and succinic acid (see Fulcher; U.S. Pat. No. 4,582,927; Issued Apr. 15, 1986); liquid triglycerides of alpha-branched chain carboxylic acids (see Whyte; U.S. Pat. No. 3,579,548; Issued May 18, 1971); liquid ethers and ether esters containing the neopentyl moiety (see Minich; U.S. Pat. No. 2,962,419; Issued Nov. 29, 1960); liquid fatty polyethers of polyglycerol (See Hunter et al; U.S. Pat. No. 3,932,532; Issued Jan. 13, 1976); liquid alkyl glycoside fatty acid polyesters (see Meyer et al; U.S. Pat. No. 4,840,815; Issued Jun. 20, 1989); liquid polyesters of two ether linked hydroxypolycarboxylic acids (e.g., citric or isocitric acid) (see Huhn et al; U.S. Pat. No. 4,888,195; Issued Dec. 19, 1988); liquid esters of epoxide-extended polyols (see White et al; U.S. Pat. No. 4,861,613; Issued Aug. 29, 1989); as well as liquid polydimethyl siloxanes (e.g., Fluid Silicones available from Dow Corning). All of the foregoing patents relating to the liquid nondigestible oil component are incorporated herein by reference.

Preferred liquid nondigestible oils are the liquid polyol fatty acid polyesters that comprise liquid sugar fatty acid polyesters, liquid sugar alcohol fatty acid polyesters, and mixtures thereof. The preferred sugars and sugar alcohols for preparing these liquid polyol polyesters include erythritol, xylitol, sorbitol, and glucose, with sucrose being especially preferred. The sugar or sugar alcohol starting materials for these liquid polyol polyesters are preferably esterified with fatty acids containing from 8 to 22 carbon atoms, and most preferably from 12 to 18 carbon atoms. Suitable naturally occurring sources of such fatty acids include corn oil fatty acids, cottonseed oil fatty acids, peanut oil fatty acids, soybean oil fatty acids, canola oil fatty acids (i.e. fatty acids derived from low erucic acid rapeseed oil), sunflower seed oil fatty acids, sesame seed oil fatty acids, safflower oil fatty acids, fractionated palm oil fatty acids, palm kernel oil fatty acids, coconut oil fatty acids, tallow fatty acids, and lard fatty acids.

The nondigestible polyol fatty acid polyesters that are liquid are those which have minimal or no sol ids at body temperatures (i.e., 98.6° F., 37° C.). These liquid polyol polyesters typically contain fatty acid ester groups having a high proportion of $C_{12}$ or lower fatty acid radicals or else a high proportion of $C_{18}$ or higher unsaturated fatty acid radicals. In the case of those liquid polyol polyesters having high proportions of unsaturated $C_{18}$ or higher fatty acid radicals, at least about half of the fatty acids incorporated into the polyester molecule are typically unsaturated. Preferred unsaturated fatty acids in such liquid polyol polyesters are oleic acid, linoleic acid, and mixtures thereof.

The following are nonlimiting examples of specific liquid polyol polyesters suitable for use in the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, the glucose tetraesters of coconut oil or unsaturated soybean oil fatty acids, the mannose tetraesters of mixed soybean oil .fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

The liquid polyol polyesters suitable for use in the compositions herein can be prepared by a variety of methods known to those skilled in the art. These methods include: transesterification of the polyol (i.e. sugar or sugar alcohol) with methyl, ethyl or glycerol fatty acid esters containing the desired acid radicals using a variety of catalysts; acylation of the polyol with a fatty acid chloride; acylation of the polyol with a fatty acid anhydride; and acylation of the polyol with the desired fatty acid, per sec. (See, for example, U.S. Pat. Nos. 2,831,854, 3,600,186, 3,963,699, 4,517,360 and 4,518, 772, all of which are incorporated by reference. These patents all disclose suitable methods for preparing polyol fatty acid polyesters.)

C. Solid Polyol Polyester Component

A second key component of the nondigestible fat compositions herein comprises relatively small nondigestible solid particles of certain polyol polyester material that are dispersed in liquid nondigestible oil to control or prevent passive oil loss. These particles can be in variety of forms and shapes, including spherulitic, platelet-like, filament-like, or rod-like, or combinations of these various shapes, but are typically spherulitic or platelet-like. The thickness of these particles is typically about 1 micron or less. Thinner particles, however, are preferred from the standpoint of providing more efficient passive oil loss control of the liquid nondigestible oil component of the compositions herein. Accordingly, these particles preferably have a thickness of about 0.1 micron or less, more preferably about 0.05 microns or less. These solid particles also have a complete melting point above about 37° C., preferably above about 50° C., more preferably above about 60° C.

The polyol polyester material which forms these nondigestible particles should have a complete melting point as measured by the Differential Scanning Calorimetry (DSC) described hereinafter in the Analytical Methods section which is sufficiently high such that the nondigestible particles themselves will have the hereinbefore specified melting point characteristics when such particles are dispersed in the liquid nondigestible oil. For example, a polyol polyester material having a complete melting point right at 37° C. may not form solid particles having a complete melting point above about 37° C. when such particles are dispersed in the liquid nondigestible oil. Thus, in some cases, the complete melting point of the neat polyol polyester material may have to be slightly higher than 37° C., e.g., about 40° C. or higher, in order to form sol id particles having a complete melting point of 37° C. when such particles are combined with the liquid nondigestible oil.

The nondigestible particles can generally be dispersed as discrete, unaggregated entities in the liquid nondigestible oil. However, these nondigestible particles can also cluster together to form much larger aggregates which are dispersed in the liquid nondigestible oil. This is particularly true of those nondigestible particles that are platelet-like in form. Aggregates of platelet-like nondigestible particles typically assume a spherulitic shape that is porous in character and thus capable of entrapping significant amounts of liquid nondigestible oil. It is believed that this porous structure and its concomitant ability to entrap large amounts of liquid nondigestible oil is why these aggregated, platelet-like particles, while not as efficient as the particles in unaggregated form, can provide very effective and efficient passive oil loss control.

The nondigestible particles for use in the compositions herein comprises certain solid polyol polyesters which have their ester group-forming fatty acid radicals selected so that the polyol backbone does not contain all of a single type of ester group. Generally, these polyol polyesters contain two basic types of ester groups. These are (i) groups formed from certain long chain saturated fatty acid radicals, and (ii) groups formed from acid radicals which are "dissimilar" to the long chain saturated fatty acid radicals. When these "dissimilar" fatty acid and/or organic acid radicals are esterified onto a polyol that contains or will contain long chain saturated fatty acid radicals, they will introduce diverse esterification into the resulting polyol polyester molecule, thereby altering the crystal structure as these molecules pack together. This diverse esterification can be due to differences in length of the ester-forming radicals (e.g., short chain versus long chain), or other steric factors, e.g., branched chain versus straight chain, unsaturated chain versus saturated chain, aromatic versus aliphatic chain, etc. Polyol polyesters containing these "long chain" and "dissimilar" ester groups are called "diversely esterified polyol polyesters".

a) Long Chain Saturated Fatty Acid Component of the Diversely Esterified Polyol Polyester Oil Loss Control Particles The ester groups of the diversely esterified nondigestible polyol polyester particles must include those formed from certain long chain saturated fatty acid radicals. Suitable long chain saturated fatty acid radicals comprise those which contain from 20 to 26, most preferably 22, carbon atoms. The long chain saturated fatty acid radicals can be used singly, or in mixtures with each other, in all proportions. In addition, straight chain (normal) fatty acid radicals are typically used as the long chain saturated fatty acid radicals which form the ester groups of the diversely esterified polyol polyester. Examples of suitable long chain fatty acid radicals include eicosanoate (arachidate), docosanoate (behenate), tetraconsanoate (lignocerate), and hexaconsanoate (cerotate).

b) Dissimilar Ester-Group Forming Component of the Diversely Esterified Polyol Polyester Oil Loss Control Particles The ester groups of the diversely esterified nondigestible polyol polyester particles must also include those formed from certain dissimilar acid radicals as hereinafter defined. Such dissimilar radicals can comprise $C_{12}$ or higher unsaturated fatty acid radicals or $C_2$–$C_{12}$ saturated fatty acid radicals or mixtures thereof or can be of the aromatic ester-forming type, or other types such as ultra-long chain or various branched cyclic or substituted acid radicals. No matter what type of dissimilar acid radical is utilized to form the diversely esterified polyol polyester oil loss control particles herein, such particles should not consist solely of diversely esterified solid polyol polyesters where the dissimilar ester-forming acid radicals comprise $C_{12}$ or higher unsaturated fatty acid radicals, $C_2$–$C_{12}$ saturated fatty acid radicals or mixtures thereof. Nondigestible particles used in the fat compositions of the present invention should preferably comprise no more than about 80%, and typically no more than 60%, of such diversely esterified solid polyol polyesters having these particular long chain unsaturated and/or short chain saturated fatty acid radicals as the dissimilar acid radical substituent.

i) Long Chain Unsaturated Radicals

A preferred class of "dissimilar" acid radicals comprises long chain unsaturated fatty acid radicals. Suitable long chain unsaturated fatty acid radicals contain at least 12, preferably from 12 to 26, more preferably from 18 to 22, most preferably 18 carbon atoms.

Examples of suitable long chain unsaturated fatty acid radicals for use in forming diversely esterified polyol polyesters include monounsaturated fatty acid radicals such as lauroleate, myristoleate, palmitoleate, oleate, elaidate, and erucate, and polyunsaturated radicals such as linoleate, arachidonate, linolenate, eicosapentaenoate, and docosahexaenoate. In terms of oxidative stability, the monounsaturated and diunsaturated fatty acid radicals are preferred.

ii) Short Chain Saturated Radicals

Another preferred class of "dissimilar" acid radicals comprises short chain saturated fatty acid radicals. Suitable short chain saturated fatty acid radicals contain from 2 to 12, preferably from 6 to 12, and most preferably 8 to 12, carbon atoms. Examples of suitable short chain saturated fatty acid radicals are acetate, butyrate, hexanoate (caproate), octanoate (caprylate), decanoate (caprate), and dodecanoate (laurate).

iii) Aromatic Dissimilar Ester-Forming Radicals

Another suitable class of dissimilar ester groups comprises those formed from aromatic radicals. Aromatic radicals can be derived from a wide variety of aromatic compounds including benzoic compounds such as benzoic acid or toluic acid; amino benzoic compounds such as aminobenzoic and aminomethyl benzoic acids; hydroxybenzoic compounds such as hydroxybenzoic, vanillic and salicylic acids; methoxybenzoic compounds such as anisic acid; acetoxyphenylacetic compounds such as acetylmandelic acid; halobenzoic compounds such as chlorobenzoic, dichlorobenzoic, and fluorobenzoic acids. Other aromatic ester-forming radicals may also be employed such as acetyl benzoic, cumic, phenylbenzoic, and nicotinic; and polycyclic aromatic radicals including fluorene carboxylic, and indole carboxylic. These aromatic type dissimilar acid radicals can be used singly, or in mixtures with each other, in all proportions.

iv) Other Dissimilar Ester-Forming Radicals

Various other ester-forming radicals can also serve as those which form the dissimilar ester groups of the diversely esterified polyol polyester particles used herein. Such other radicals can be branched chain alkyls, e.g., methyl alkyl radicals such as methyl stearic, isobutyric, and isovaleric; ultra-long chain saturated or unsaturated radicals including tricotanoic and tricontenoic; cyclic aliphatic radicals including cyclobutane carboxylic, cyclopentane carboxylic, cyclohexane carboxylic, cyclohexane acetic, and hydroxycyclic such as ascorbic; polycyclical iphatics such as abietic; polymeric ester-forming acids such as polyacrylic and dimer fatty acid; and alkyl chain esters with "functional" groups attached including haloalkyl compounds such as chlorostearic, chlorocaprylic, chloroacetic, bromostearic, bromocaprylic, and bromoacetic; aminoalkyl compounds such as aminocaprylic and aminostearic; phenoylalkyl compounds such as benzoylbutyric; and phenylalkyl compounds such as phenyl acetic. These "other" dissimilar radicals can also be used singly, or in mixtures with each other, in all proportions.

c) Preparation of Diversely Esterified Polyol Polyesters

The diversely esterified polyol polyesters of the type hereinbefore described can be prepared by esterifying the desired polyol with the requisite type of ester-forming radicals. Mixed fatty acid radicals from oils which contain substantial amounts of the desired dissimilar and/or long chain saturated fatty acids can be used as the sources of fatty acid radicals in preparing the solid polyol polyesters used in the present invention. The mixed fatty acids from such oils should preferably contain at least about 30% (preferably at least about 50%, and most preferably at least about 80%) of the desired dissimilar and/or long chain saturated fatty acids. For example, palm kernel oil fatty acids can be used instead of a mixture of the respective pure saturated fatty acids having from 8 to 12 carbon atoms. Similarly, rapeseed oil fatty acids or soybean oil fatty acids can be used instead of a mixture of the respective pure monounsaturated and polyunsaturated fatty acids having 12 to 26 carbon atoms, and hardened (i.e., hydrogenated) high erucic rapeseed oil fatty acids can be used in place of a mixture of the respective pure long chain saturated fatty acids having from 20 to 26 carbons. Preferably, the $C_{20}$ and higher acids (or their derivatives-e.g., methyl esters) are concentrated, for example, by distillation.

The diversely esterified solid nondigestible polyol polyester particles used herein and prepared from the various sources of acid radicals as outlined hereinbefore will generally contain at least about 15%, preferably at least about 30%, more preferably at least about 50%, and most preferably at least about 80%, of the long chain saturated fatty acid radicals along with at least some of the dissimilar acid radicals. In the diversely esterified polyol polyester materials used herein, the molar ratio of dissimilar radicals to long chain saturated fatty acid radicals can range from about 0.1:7.9 to about 3:5, preferably from about 0.5:7.5 to about 2:6, more preferably from about 1:7 to about 1.5:6.5. A typical suitable molar ratio of dissimilar acid radicals to long chain saturated fatty acid radicals is about 1:7.

The diversely esterified solid polyol polyester materials useful herein can be made according to prior known methods for preparing polyol polyesters. Since the sucrose polyesters are the preferred solid polyol polyesters for use in the present invention, such preparation will be exemplified primarily by these materials. One such method of preparation comprises reacting the acid chlorides or acid anhydrides of the desired ester-forming acids, or the acids per se, with sucrose, preferably using a sequential esterification process. In this sequential esterification process, sucrose is initially partially esterified with the dissimilar acid chlorides, followed by complete or substantially complete esterification of this initial reaction product with the long chain saturated fatty acid chloride, in that order, or in reverse order. (See Letton; European Patent 311,154; Published Apr. 12, 1989, herein incorporated by reference).

Another method for preparing these diversely esterified solid polyol polyesters is by the process of reacting methyl esters of the desired ester-forming acids with sucrose in the presence of a fatty acid soap and a basic catalyst such as potassium carbonate. (See, Jandacek et al; U.S. Pat. No. 4,797,300; Issued Jan. 10, 1989; Rizzi et al; U.S. Pat. No. 3,963,699; Issued Jun. 15, 1976; Volpenhein; U.S. Pat. No. 4,518,772; Issued May 21, 1985; and Volpenhein; U.S. Pat. No. 4,517,360; Issued May 14, 1985, and Letton; European Patent 311,154; Published Apr. 12, 1989, all of which of which relate to polyol polyester synthesis.) When using the methyl ester route to prepare these diversely esterified solid polyol polyesters having mixed dissimilar acid radicals and long chain saturated fatty acid radicals, the octaester of one of the types of acids (e.g., dissimilar acids, or long chain saturated fatty acids) can be prepared first, followed by partial interesterification of this initial reaction product with the methyl ester of the other type of acid. In a preferred way of practicing this methyl ester process, the methyl esters of the long chain saturated fatty acids are reacted with sucrose in a first stage at about 135° C. to obtain partial esters of sucrose. The methyl esters of the dissimilar acids are then added to the reaction and the temperature is dropped to 90°–120° C., as necessary (and reflux, if required) to achieve the desired degree of esterification.

When using the methyl ester route to prepare these diversely esterified solid polyol polyesters having mixed dissimilar acid and long chain saturated fatty acid radicals, the dissimilar and long chain saturated methyl esters are blended in the desired ratio and reacted with sucrose by transesterification to obtain the sucrose esters of mixed dissimilar/long chain saturated fatty acids.

D. Preparation of Nondigestible Fat Compositions Which Exhibit Minimal Passive Oil Loss To prepare the nondigestible fat compositions herein which exhibit improved passive oil loss control, the liquid nondigestible oil is combined with the particles of the solid polyol polyesters hereinbefore described. The polyol polyester particles are used in an amount sufficient to control or prevent passive oil loss. What constitutes "an amount sufficient to control or prevent passive oil loss" for any given fat composition depends upon the particular solid polyol polyester utilized therein, the particular passive oil loss control benefits desired, and the level of waxiness mouth impression which can be tolerated for the particular end product use of the nondigestible fat composition which is formulated. Typically, the nondigestible fat composition so formed will comprise from about 60% to about 99% of the liquid nondigestible oil and from about 1% to about 40% of the solid polyol polyester particles. Preferably, this mixture comprises from about 80% to about 99% liquid nondigestible oil and from about 1% to about 20% of the solid polyol polyester particles, more preferably from about 85% to about 99% liquid nondigestible oil and from about 1% to about 15% of the solid polyol polyester particles, even more preferably from about 90% to about 99% liquid nondigestible oil and from about 1% to about 10% of the solid polyol polyester particles, and most preferably from about 95% to about 99% liquid nondigestible oil and from about 1% to about 5% of the solid polyol polyester particles. The use of higher levels of liquid nondigestible oil (i.e., lower levels of solid polyol polyester particles) may be desirable from the standpoint of reducing waxiness impression left by the solid components of the nondigestible fat compositions herein. However, higher levels of solid polyol polyester particles (i.e., lower levels of liquid nondigestible oil ) are desirable from the standpoint of controlling or preventing passive oil loss associated with the ingestion of compositions containing such liquid nondigestible oils.

The combination of liquid nondigestible oil and solid polyol polyester particles are typically prepared by simply mixing these two components together, by heating the mixture until the solid polyol polyester material dissolves in the oil, and by then cooling the mixture to a suitable crystallization temperature, e.g., room temperature.

The specific size of the polyol polyester particles thus formed in the fat compositions herein will be dependent upon the rate at which the heated combination of oil and dissolved solid is cooled. As used herein, cooling rate is defined as the temperature differential between (a) the heated oil/dissolved solid combination and (b) the cooled crystallized liquid/solid particle combination, divided by the time taken to create this temperature differential. Generally the greater the cooling rate employed in forming the fat compositions herein, the smaller will be the particles of solid polyol polyester material dispersed in such compositions. Desirable cooling rates for use in forming the fat compositions herein are typically greater than 0.6° C./min. (1° F./min.), preferably greater than 2.8° C./min. (5° F./min.), more preferably greater than 5.6° C./min. (10° F./min), and most preferably greater than 27.8° C./min. (50° F./min.). When the nondigestible fat compositions herein are to be formed in situ, for example, within a food product of which they form a part, then the type and concentration of the fat composition components should be selected so that the cooling profile experienced by the food product will result in formulation of the desired amount and size of the solid polyol polyester particles within the food product.

The formation of thin nondigestible particles according to the present invention provides especially efficient passive oil loss control for the resulting fat composition. Such efficiency permits a reduction in solids content of the nondigestible fat to relatively low levels (e.g., to from about 1 to about 15%). This reduction in solids level required for passive oil loss control, together with the minimal/no change in solid content between typical room and body temperatures, leads to nondigestible fats having a less waxy tasting impression.

Both the liquid nondigestible oil and the solid nondigestible polyol polyester components, as well as the respective concentrations, are selected in order to provide nondigestible fat compositions having a certain set of physical characteristics. In particular, the nondigestible fats of the present invention should exhibit a relatively flat Solid Fat Content (SFC) profile slope across the temperature range of from typical room temperature to body temperature, i.e., from 70° F. to 98.6° F. The SFC profile slope between these temperatures should be from 0 to about −0.75 % solids/°F., preferably from 0 to about −0.5 % solids/°F., more preferably from 0 to about −0.3 % solids/°F., most preferably from 0 to about −0.1% solids/°F. The method for determining the SFC profile slope of the fat compositions herein is described hereinafter in the Analytical Methods section.

E. Food Products with Nondigestible Fat Compositions

The nondigestible fats of the present invention can be used in various edible fat-containing products including foods, beverages, and pharmaceuticals, either alone or in combination with other materials such as digestible fats and oils. In particular, the nondigestible fats of the present invention can be optionally formulated with a digestible triglyceride fat or oil. Generally, these formulations can comprise from about 10% to 100% nondigestible fat and from 0% to about 90% digestible triglyceride fat or oil. Preferably, these formulations comprise from 35% to 100%, more preferably from about 50% to about 100% and most preferably from about 75% to about 100% nondigestible fat, and from 0% to about 65%, more preferably from 0% to about 50%, and most preferably from 0% to about 25%, digestible triglyceride fat or oil. Because of the potential caloric impact of these triglyceride fats or oils, it is desirable to minimize the level at which they are combined with the nondigestible fat compositions of the present invention.

As used herein, the term "triglyceride oil" refers to those triglyceride compositions which are fluid or liquid at room temperature, i.e., at 25° C. Although not a requirement, the triglyceride oils useful in the present invention can include those which are fluid or liquid below 25° C. These triglyceride oils consist primarily of triglyceride materials, but can also include residual levels of other components such as mono- and diglycerides. To remain fluid or liquid at temperatures below 25° C., the triglyceride oil contains a minimal amount of glycerides having melting points higher than about 25° C. so as to limit the solids increase when the triglyceride oil is cooled. It is desirable that the triglyceride oil be chemically stable and resistant to oxidation.

Suitable triglyceride oils can be derived from naturally occurring liquid vegetable oils such as cottonseed oil, soybean oil, safflower oil, corn oil, olive oil, coconut oil, palm kernel oil, peanut oil, rapeseed oil, canola oil (i.e., rapeseed oil low in erucic acid), sesame seed oil, sunflower seed oil, and mixtures thereof. Also suitable are liquid oil fractions obtained from palm oil, lard and tallow by, for example, graining or directed interesterification, followed by separation of the oils. Oils predominating in glycerides of unsaturated acids can need some hydrogenation to maintain flavor, but care should be taken not to greatly increase the amount of glycerides melting above 25° C. When oils are selected which have a larger amount of solids melting between 25° and 40° C. than are desirable, it can be necessary to separate out the solids. For example, refined and slightly hydrogenated soybean oil is suitable, as well as refined cottonseed oil.

As used herein, the term "triglyceride fat" refers to those triglyceride compositions which are solid or plastic above about 25° C. These solid or plastic fats can be derived from plants or animals or can be edible synthetic fats or oils. For example, animal fats such as lard, tallow, oleo oil, oleo stock, oleo stearin and the like which are solid at room temperature can be utilized. Also, triglyceride oils, e.g. unsaturated vegetable oils, can be converted into plastic fats by partial hydrogenation of the unsaturated double bonds of fatty acid constituents of the oil followed by conventional chilling and crystallization techniques or by proper mixture with sufficient triglycerides which are solid at room temperature to form a rigid interlocking crystalline structure which interferes with the free-flowing properties of the liquid oil. See Purves et al; U.S. Pat. No. 3,355,302; Issued Nov. 28, 1967, and Darragh et al; U.S. Pat. No. 3,867,556; Issued Feb. 18, 1975 (both incorporated herein by reference), for further examples of solid or plastic fats. Because the solid or plastic fats add an appreciable level of solids, their inclusion can cause adverse effects on the organoleptic properties, in particular waxiness, of the edible fat-containing products of the present invention.

Triglyceride fats and oils useful in the nondigestible fats of the present invention can include certain triglycerides in which one, two or three of the OH groups of the glycerol molecule have been substituted with acetyl, propionyl, butyryl, caproyl, caprylyl, or capryl radicals, and the remaining OH groups of the glycerol molecule (if any) have been substituted with acyl radicals of saturated or unsaturated fatty acids having from 12 to 24 carbon atoms.

The nondigestible fat materials of this invention can also be used in combination with reduced calorie medium chain and mixed medium/long chain triglycerides. See, for example, Ehrman et al.; U.S. Pat. No. 4,888,196; issued Dec. 19, 1989 and Seiden; European Patent 322,037; Published Jun. 28, 1989.

The nondigestible fat compositions of the present invention can be used in or as shortening and oil products. The shortening and oil products can be used in frying applications such as preparation of french fried potatoes, potato chips from potato slices or fabricated potato pieces, potato sticks, corn chips, tortilla chips, donuts, chicken, fish, and fried pies (e.g. turnovers). The shortening and oil products can also be used in preparing baked goods in any form, such as mixes, shelf-stable baked goods, and frozen baked goods, including, but not limited to, cakes, granola bars, brownies, muffins, bar cookies, wafers, biscuits, pastries, pies, pie crusts, and cookies, including sandwich cookies, chocolate chip cookies, particularly storage stable dual-texture cookies as disclosed in Hong et al; U.S. Pat. No. 4,455,333; Issued Jun. 19, 1984. These baked goods can contain fruit, cream, or other fillings. Other baked goods uses include breads and rolls, crackers, pretzels, pancakes, waffles, ice cream cones and cups, yeast-raised bake goods, pizza and pizza crust, and baked farinaceous snack products and other baked salted snacks.

Other edible fat-containing products which may contain the nondigestible fat compositions of the present invention include ice cream, frozen desserts, cheese, cheese spreads, meats, meat analogs, chocolate confections, salad dressings, mayonnaise, margarine, spreads, sour cream, yogurt, coffee creamer, peanut butter, extruded snacks such as corn curls, corn puffs, pellet snacks, half products or other extruded snacks based on corn or other cereal grains such as wheat, rice and the like, roasted nuts and beverages such as milkshakes.

Edible fat-containing products which can contain the nondigestible fat composition of this invention include noncaloric or reduced calorie sweeteners alone or in combination with bulking agents. These noncaloric or reduced calorie sweeteners include, but are not limited to, aspartame, saccharin, alitame, thaumatin, dihydrochalcones, acesulfame, and cyclamates.

Bulking or bodying agents which can be useful in edible fat-containing products containing the nondigestible fat compositions herein include partially or wholly nondigestible carbohydrates, for example, polydextrose and cellulose or cellulose derivatives, such as D, L- sugars, carboxymethylcellulose, carboxyethylcellulose, hydroxypropylcellulose, methylcellulose, hydroxypropyl methylcellulose, and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

The edible fat-containing products containing the nondigestible fat compositions herein can also include dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers can be used, such as psyllium and fibers from whole citrus peel, citrus albedo, sugar beets, citrus pulp and vesicle solids, apples, apricots, and watermelon rinds.

These dietary fibers can be in a crude or purified form. The dietary fiber used can be of a single type (e.g., cellulose), a composite dietary fiber (e.g., citrus albedo fiber containing cellulose and pectin), or some combination of fibers (e.g., cellulose and a gum). The fibers can be processed by methods known to the art.

The nondigestible fat compositions of the present invention can also be fortified with vitamins and minerals, particularly the fat-soluble vitamins. The fat-soluble vitamins include vitamin A, vitamin D, and vitamin E and their precursors. (See Mattson; U.S. Pat. No. 4,034,083; Issued Jul. 5, 1977, herein incorporated by reference which discloses fat-soluble vitamins useful in fortifying polyol fatty acid polyesters.)

Various other ingredients typically present in fat products can also be included in the nondigestible fats of the present invention. These other ingredients include stabilizers to help protect against oxidative deterioration at high temperatures. Silicone oils, particularly methyl and ethyl silicone oils, are useful for this purpose. Methyl silicones have also proven effective in reducing the rate of oil polymerization during frying. Other additives typically included in fat products such as minor amounts of optional flavorings, emulsifiers, anti-spattering agents, anti-sticking agents, anti-oxidants, or the like can also be present.

F. Alternate Utility for the Diversely Esterified Solid Polyol Polyester Particles It has been found that the diversely esterified solid polyol polyester particles useful as oil loss control agents in the nondigestible fat compositions herein are also effective for use as thickening agents in conventional digestible triglyceride oils or oil-containing products. Accordingly, these solid polyol polyester particles can be used as "thickening agents" or "hardstocks" by blending them in amounts of about 1% to about 20% (preferably from about 1% to about 15%, more preferably from about 1% to about 10%, most preferably from about 1% to about 8%) with liquid digestible oils in the formulation of cooking and salad oils or semi-solid food products such as shortenings, as well as other food products which contain a combination of fat and non-fat ingredients, e.g., margarines, mayonnaise, frozen dairy desserts and the like. The oils for these compositions can comprise conventional digestible triglyceride oils such as cottonseed, corn, canola or soybean, or medium or medium and long chain triglycerides.

G. Analytical Methods

A number of parameters used to characterize elements of the present invention are to be quantified by particular experimental analytical procedures. Each of these procedures is described in detail as follows:

1. Fatty Acid Composition of Polyol Polyesters

The fatty acid composition (FAC) of the polyol polyesters is determined by gas chromatography, using a Hewlett-Packard Model S712A gas chromatograph equipped with a flame ionization detector and a Hewlett-Packard Model 7671A automatic sampler.

The method is applicable to methyl esters of fatty acids having 8 to 24 carbon atoms and to animal fats, vegetable oils, marine oils and fatty acids after their conversion to methyl esters. The method permits quantitative separation of mixtures containing saturated and unsaturated methyl esters. The conditions specified in this method are not suitable for determining epoxy or oxidized fatty acids or fatty acids that have been polymerized.

Apparatus 1.
1. The gas chromatograph, which is commercially available, should have as a minimum the following characteristics—
   (a) Column oven, capable of heating the column to at least 220° C. and of maintaining the desired temperature to within ±1° C.
   (b) Sample inlet port with minimum dead space which is independently heated to a temperature 20°–50° C. higher than column temperature.
   (c) Detectors, thermal conductivity (TC) or flame ionization (FID), separately thermostated, which can be maintained at or above column temperature.
2. Recorder—If the recorder curve is to be used to calculate the composition of the mixture analyzed, an electronic recorder of high precision is required. The characteristics of the recorder should be—
   Rate of response below 1.0 seconds (the rate of response is the time taken for the recording pen to pass from 0 to 90 percent following the momentary introduction of a 100 percent signal).
   (b) Chart paper width, 25 cm (10 inches) minimum.
   (c) Chart paper speed, 25–100 cm/hr (10–40 inches/hour).
3. Integrator or Calculator (optional)—Rapid and accurate calculation can be performed with the help of an electronic integrator or calculator. This must give a linear response with adequate sensitivity, and baseline correction should be consistent with good chromatographic practice. Horizontal, non-horizontal and tangential baseline correction must be controlled by selectable electronic peak logic.
4. Syringe, maximum capacity 10 μL, graduated in 0.1 μL.
5. Chromatographie Column—
   (a) The column must be constructed of a material inert to the substances to be analyzed, glass, or failing that, stainless steel (see Notes, 1), with a length of 1 to 3 m and an internal diameter of 2 to 4 mm.
   (b) Packing support, acid-washed and silanized diatomaceous earth, or other suitable inert support with a narrow range (25 gin) of grain size between the limits of 60–120 mesh (125–250 μm).
   (c) Stationary phase, polyester type of polar liquid (diethylene glycol polysuccinate, butanedial polysuccinate, ethylene glycol polyadipate), or any liquid (e.g., cyanosilicones), meeting the requirements below. The stationary phase should amount to 5–20 percent of the packing. A nonpolar stationary phase, such as methyl silicone, fluid or gum, can be used for separations of fully saturated materials.

Reagents:
1. Gases—
   (a) Carrier gas for TC detector, helium, minimum purity 99.95 mol %; for FID, helium, nitrogen, or argon, minimum purity 99.95 mol %.
   (b) FID, hydrogen, minimum purity 99.95 mol %; air, dry (dew point –75F maximum) and hydrocarbon free (less than 2 ppm hydrocarbons equivalent $CH_4$).

2. References Standards—A mixture of methyl esters, or the methyl esters of an oil of known composition, preferably similar to that of the fatty matter to be analyzed. Reference mixtures simulating most fats and oils may be obtained from—Applied Science Laboratories, Inc., P.O. Box 440, State College, Pa. 16801. Supelco, Inc., Supelco Park, Bellefonte, Pa. 16823. Nu Chek Prep, Inc., P.O. Box 172, Elysian, Minn. 56028. Analabs, Inc., 80 Republic Drive, North Haven, Conn. 06473. Alltech Associates, Inc., 2501 Waukegan Road., Deerfield, Ill. 60015.

Preparation of Methyl Esters:

AOCS Official Method Ce 2-66 is recommended.

Procedure:

1. Conditioning a new column while disconnected from detector by holding it about 10° C. above its operating temperature with flow of inert gas at 20–60 mL/min. for approximately 16 hours and then an additional 2 hours at 20° C. above its operating temperature. In no case exceed the manufacturer's recommended maximum temperature.

2. Determining optimal operating conditions—

(a) In selecting the test conditions, the following variables must be taken into account: length and diameter of the column, temperature of the column, carrier gas flow, resolution required, size of the sample for analysis and time of analysis. The size of the sample should be chosen so that the assembly of detector and electrometer gives a linear response. As a rule, the following figures will lead to the desired results, viz., at least 2,000 theoretical plates for methyl stearate and its elution within about 15 minutes:

| Internal Diameter of Column | Carrier Gas Supply |
|---|---|
| 2 mm | 15–25 ml/min |
| 3 mm | 20–40 ml/min |
| 4 mm | 40–60 ml/min |

| Concentration of Stationary Phase | Temperature |
|---|---|
| 5 percent | 175° C. |
| 10 percent | 180° C. |
| 15 percent | 185° C. |
| 20 percent | 185° C. |

(b) Where the apparatus allows, the injection port should be at a temperature of about 250°–275° C. and the detector at a temperature equal to, or higher than, that of the column.

(c) The flow of hydrogen to the flame ionization detector is, as a rule, about 0.5 to 1 times that of the carder gas, and the flow of air about 5 to 10 times that of the hydrogen.

3. Determining the efficiency and the resolution—

(a) Carry out the analysis of a mixture of methyl stearate and oleate in about equivalent proportions (e.g., methyl esters from cocoa butter). Choose the size of the sample, the temperature of the column and the carder gas flow so that the maximum of the methyl stearate peak is recorded about 15 minutes after the solvent peak and rises to three-quarters of the full scale. Calculate the number of theoretical plates n (efficiency) by the formula n—

$$n = 16(dR_1/w_1)^2$$

and the resolution, R, by the formula R—

$$R = 2\Delta/(w_1 + w_2)$$

where—

$dR_1$ is the retention distance, measured in mm, from the start to the maximum peak of methyl stearate.

$w_1$ and $w_2$ are the widths, in nun, of the peaks for methyl stearate and methyl oleate, measured between the points of intersection of the tangents at the inflection points of the curve with the base-line.

$\Delta$ is the distance between the respective peak maxima for methyl stearate and oleate.

(b) Operating conditions to be selected are those which will afford at least 2,000 theoretical plates for methyl stearate, and a resolution at least 1.25. Additionally, linolenic acid ($C_{18:3}$) ester should be separable from archidic acid ($C_{20:0}$) and gadoleic acid ($C_{20:1}$) esters.

(c) As a rule, the operating conditions will be those defined above. Nevertheless, it is possible to work with a lower column temperature where the determination of acids below $C_{12}$ is required, or at a higher temperature when determining fatty acids above $C_{20}$.

(d) On occasion, it is possible to employ temperature programming in both the previous cases. For example, if the sample contains the methyl esters of fatty acids below $C_{12}$, inject the sample at 100° C. column temperature and immediately raise the temperature at a rate of 4°–8° C./minute to the optimum. In some cases, the two procedures can be combined. After the programmed heating, continue the elution at a constant temperature until all the components have been eluted. If the instrument does not employ programmed heating, work at two fixed temperatures between 100° C. and 195° C. Liquid phase characteristics will determine the starting temperature or the upper temperature if the analysis is performed iso-thermally.

4. Analysis—

(a) The sample for examination should be 0.1–2 μL of the solution of methyl esters obtained according to AOCS Official Method Ce 2-66. In the case of esters not in solution, prepare an approximate 1–10% solution and inject 0.1–1 μL of this solution.

(b) If the object is to determine constituents present only in trace amounts, the sample size may be increased (up to tenfold).

Calculations:

1. Identification of Peaks—

(a) Analyze the reference standard mixture of known composition under the same operating conditions as those employed for the sample, and measure the retention distances (or retention times) for the constituent esters. Construct graphs showing the logarithm of the retention distance (or retention time) as a function of the number of carbon atoms of the acids; under isothermal conditions, the graphs for straight chain esters of the same degree of unsaturation should be straight lines. These straight lines are approximately parallel.

(b) Identify the peaks for the sample from these graphs, by interpolation if necessary.

(c) It is necessary to avoid conditions which permit masked peaks, i.e., where the resolution is not adequate to separate two components.

2. Quantitative Analysis—

(a) Apart from exceptional cases, assume that the whole of the components of the sample are represented on the chromatogram, so that the total of the areas under the peaks represents 100% of the consistuents (total elution).

(b) If the equipment includes an integrator, use the figures obtained therefrom. If not, determine the area under each peak by multiplying the height by the breadth at mid-height-and, where necessary, take into account the various attenuations used during the recording.

(c) For the general case, in which significant amounts of components below $C_{12}$ are absent, calculate the content of a particular constituent (expressed as percent of methyl esters) by determining the percentage represented by the area of the corresponding peak relative to the sum of the areas of all the peaks.

Area percent of the component i expressed as methyl ester=

$$\frac{A_i}{\Sigma A_i} \times 100$$

Where—

$A_i$=area of the peak corresponding to component i.

$\Sigma A_i$=sum of the areas under all the peaks.

(d) Correction factors, particularly in the presence of acids below $C_{12}$, of acids with secondary groups, or when using a TC detector, must be used to convert the percentages of peak areas into mass-percentages of the components. Determine the correction factors with the help of a chromatogram derived from the analysis of a reference mixture of methyl esters of known composition under operating conditions identical with those used for the sample.

For this reference mixture:

Weight percent (m/m) of component i=

$$\frac{B_i}{\Sigma B_i} \times 100$$

Where—

$B_i$=mass of component i in the reference mixture $\Sigma B_i$=total of the masses of the various components of the reference mixture.

From the chromatogram of the reference mixture, one can calculate:

$$\text{Area percent of component } i = \frac{C_i}{\Sigma C_i} \times 100$$

Where—

$C_i$=area under the peak corresponding to component i $\Sigma C_i$=sum of the area under all the peaks.

Whence—

$$\text{Correction factor } K_i = \frac{B_i \times \Sigma C_i}{C_i \times \Sigma B_i}$$

Commonly, the correlation factors are made relative to $K_{C_{16}}$ so the relative factors become:

Then the content of each component in the sample is given by:

Weight percent (m/m) of component i, expressed as methyl esters=

$$\frac{(K'_i \times A_i)}{\Sigma(K'_i \times A_i)} \times 100$$

(e) Use an internal standard, notably in determinations when all of the fatty acids are not eluted. The internal standard may be the methyl ester of the $C_{13}$ fatty acid. The correction factor for the internal standard should be determined:

Weight percent (m/m) of component i, expressed as methyl esters=

$$\frac{m_{C_{13}} \times K'_i \times A_i}{m \times K'_{C_{13}} \times A_{C_{13}}} \times 100$$

Where—

$m_{C_{13}}$=mass, in mg, of the internal standard added to sample m=mass, in rag, of the sample

*$K'_{C_{13}}$=correction factor for the internal standard relative to $K_{C_{16}}$ $A_{C_{13}}$=area of the peak corresponding to the internal standard $A_i$=area of the peak corresponding to component i $K'_i$=correction factor of component i relative to $K_{C_{16}}$ $$*K'_{C_{13}} = \frac{K_{C_{13}}}{K_{C_{16}}}$$

*Determined be adding a known amount $C_{13}$ methyl ester to the reference mixture and then following the above procedure for determining $K'_i$.

(f) Expression of the results—
  Give the results to: 3 significant figures for contents over 10%, 2 significant figures for contents between 1 and 10 percent, 1 significant figure for contents below 1 percent, i.e., with one figure beyond the decimal point in every case.

Precision:
1. Repeatability—The difference between the results of two determinations carded out on the same day by the same operator using the same apparatus for the same esters and for constituents present in excess of 5% should not exceed a relative figure of 3% of the determined value, with an absolute value of 1%. For components present in amounts of less than 5%, the repeatability in relative terms diminishes progressively as the content is reduced.
2. Reproducibility—The difference between the results obtained in two different laboratories for constituents present in excess of 5% should not exceed a relative figure of 10% of the determined value, with an absolute maximum of 3%. For constituents present in amounts less than 5%, the reproducibility in relative terms diminishes progressively as the content is reduced.

Notes:
1. If polyunsaturated components with more than three double bonds are present, they may decompose in a stainless-steel column.
2. It is recommended that chromatographers read "Standard Recommended Practice for General Gas Chromatography Procedures", ASTM Designation E260-73; "Standard Recommended Practice for Gas Chromatography Terms and Relationships", ASTM Designation E355-77; and "Standard Recommended Practice for Testing Flame Ionization Detectors Used in Gas Chromatography", ASTM Designation E594-77.

2. Ester Distribution of Sucrose Polyesters

The relative distribution of the individual octa-, hepta-, hexa- and penta- esters, as well as collectively the tetra- through mono- esters, of the sucrose polyesters can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e. an evaporative light-scattering detector). The detector response is measured and then normalized to 100%. The individual ester groups are expressed as a relative percentage.

3. Slope of Solid Fat Content (SFC) Profile of Nondigestible Fat Measured in °F.

Before determining the SFC values, a sample of the nondigestible fat is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; at 32° F. (0° C.) for 15 minutes. After tempering, the SFC values of the sample at temperatures of 50° F. (10° C.), 70° F. (21.1° C.), 80° F. (26.7° C.), 92° F. (33.3° C.), and 98.6° F. (37° C.) are determined by pulsed nuclear magnetic resonance (PNMR) after equilibration for 30 minutes at each temperature. The slope of the SFC profile in % solids/°F. is calculated by subtracting the SFC value at 70° F. (21.1° C.) from the SFC value at 98.6° F. (37° C.) and then dividing by 28.6. The method for determining SFC values by PNMR is as follows Apparatus:
1. Praxis Pulsed NMR SFC 900 Solid Fat Analyzer available from The Praxia Corporation, San Antonio, Tex., 7825 1, or equivalent.
2. Sample robes. Test robes, culture, disposable, Pyrex or Kimax glass, 10 mm OD×75 mm length without rims, with dimensions 0.380±0.005 inches OD (9.65±0.13 mm OD).
3. Oven maintained at 70° C.±2° C.
4. Corks, size 0.
5. Tissues for wiping sample robes.

Reagents:
Olive oil reference liquids having the following compositional analysis (See Notes, 2 )—

|  | Spanish | Italian |
|---|---|---|
| Iodine Value: | 84–87 | 85–88 |
| Saponification Value: | 189–195 | 192–195 |
| Fatty Acid Composition |  |  |
| $C_{16}$ | 9.5 ± 1.0 | 14.0 ± 1.5 |
| $C_{18}$ | 3.5 ± 0.5 | 2.5 ± 0.5 |
| $C_{18:1}$ | 76 ± 2.0 | 65.0 ± 3.0 |
| $C_{18:2}$ | 7.0 ± 1.5 | 14.0 ± 1.5 |
| $C_{18:3}$ | 1.0 ± 0.2 | 1.0 ± 0.2 |

Procedure:
1. Filling the sample tubes—
    (a) Heat the sample in the 70° C. oven until liquid and mix well.
    (b) Fill the sample tube with the melted sample to approximately 15 mm from the top.
    (c) Place cork in top of sample tube.
    (d) Wipe sample tube with tissue making sure outside of tubes are clean.
2. Tempering of the sample and pulsed nmr measurements
(a)
    (a) Insert sample tubes containing all samples to be measured and the reference olive oil sample into the sample tempering ports of the 60° C. probe.
    (b) Equilibrate all samples and reference oil for 30 minutes.
    (c) Set the instrument conditions as follows—

| | |
|---|---|
| Auto/Manual Switch | Auto |
| Probe/Selector | 6 |
| FID/Temp Switch | FID |
| Response | Fast |
| Variable Delay | 100 × 1 |
| Clock | 2 × 1.0 |
| Function | 90° C. |
| Program Counter | 8 |
| Gain and Instrument Background | Refer to Operators Manual |
| Probe Temperatures | Refer to Operators Manual |

(d) Insert the olive oil reference sample into the analysis port and measure the NMR reading (see Notes, 3).
  (e) Insert each sample into the analysis port and measure the NMR reading of each sample.
  (f) Transfer the reference oil and samples to the 26.7° C. probe and equilibrate for exactly 15 minutes.
  (f) Transfer the reference oil and samples to the 0° C. probe and equilibrate for exactly 15 minutes.
  (h) Transfer the reference oil and samples to the 26.7° C. probe and temper for exactly 30 minutes.
  (i) Transfer the reference oil and samples to the 0° C. probe and chill for exactly 15 minutes.
  (j) Transfer the reference oil and samples to the 10° C. probe and equilibrate for exactly 30 minutes.
  (k) Set clock to 1×1.0 an Probe Selector to 1.
  (l) Measure the NMR reading of the reference oil and samples.
  (m) Transfer the reference oil and samples to the 21.1° C. probe and equilibrate for exactly 30 minutes.
  (n) Set Probe Selector to 2.
  (o) Measure the NMR reading of the reference oil and the samples.
  (p) Transfer the reference oil and samples to the 26.7° C. probe and equilibrate for exactly 30 minutes.
  (q) Set Probe Selector to 3.
  (r) Measure the NMR reading of the reference oil and the samples.
  (s) Transfer the reference oil and samples to the 33.3° C. (or to 40.6° C.) probe and equilibrate for exactly 30 minutes.
  (t) Set Probe Selector to 4.
  (u) Measure the NMR reading of the reference oil and samples.
  (v) Transfer the reference oil and samples to the 37.8° C. (or to 40.6° C.) probe and equilibrate for exactly 30 minutes.
  (w) Set Probe Selector to 5.

(x) Measure the NMR reading of the reference oil and samples.

Calculations:

---

1. Solid Fat Content (SFC) at temperature TC =

$$\frac{\text{Reference oil at } 60° \text{ C.}}{\text{Sample at } 60° \text{ C.}} \times \frac{\text{Sample at TC}}{\text{Reference Oil TC}} \times 100$$

Example:
NMR Readings:

| | |
|---|---|
| Reference Oil at 60° C. | 105.6 |
| Sample at 60° C. | 105.4 |
| Reference Oil at T° C. (10.0) | 98.8 |
| Sample at T° C. (10.0) | 80.2 |

$$\% \text{ Solid Fat} = 100 - \frac{105.6}{105.4} \times \frac{80.2}{98.8} \times 100 = 18.67\%$$

---

Precision:

Data from the AOCS collaborative study which validated this method show the following reproducibility can be expected—

1. Within and between laboratories, separate determinations of margarine-type oils should be plus or minus one standard deviation for temperatures listed:

| | 10.0° C. | 21.1° C. | 26.7° C. | 33.3° C. | 37.8° C. |
|---|---|---|---|---|---|
| Std. dev. | 0.6 | 0.5 | 0.6 | 0.6 | 0.4 |

2. Within and between laboratories, separate determinations of plasticized shortening-type oils should be plus or minus one standard deviation for temperatures listed:

| | 10.0° C. | 21.1° C. | 26.7° C. | 33.3° C. | 37.8° C. |
|---|---|---|---|---|---|
| Std. dev. | 0.7 | 0.7 | 0.6 | 0.5 | 0.4 |

3. Within and between laboratories, separate determination of non-cocoa butter-type confectionery fats should be plus or minus one standard deviation for temperatures listed:

| | 10.0° C. | 21.1° C. | 26.7° C. | 33.3° C. | 37.8° C. |
|---|---|---|---|---|---|
| Std. dev. | 0.6 | 1.0 | 1.1 | 0.5 | 0.4 |

4. Within and between laboratories, separate determinations for unhydrogenated palm-type oils should be plus or minus one standard deviation for temperatures listed (see Notes, 4):

| | 10.0° C. | 21.1° C. | 26.7° C. | 33.3° C. | 37.8° C. |
|---|---|---|---|---|---|
| Std. dev. | 1.0 | 0.8 | 0.6 | 0.5 | 0.4 |

5. Within and between laboratories, separate determinations tristearin in olive standards should be plus or minus one standard deviations at 10° C. for the percent tristearin in olive oils listed (see Notes, 5):

| | 10.0° C. | 21.1° C. | 26.7° C. | 33.3° C. | 37.8° C. |
|---|---|---|---|---|---|
| Std. dev. | 0.2 | 0.2 | 0.4 | 0.2 | 0.1 |

Notes:

1. The basic procedure described is applicable at temperatures and times other than those specified and the Committee recognizes that sometimes such deviations are necessary. In 1989, a collaborative study effort by the AOCS NMR Technical Committee was begun to establish harmonized tempering conditions for existing NMR instruments and for other types of fats and oils. The Committee expects this study to be completed in 1991.
2. The basic procedure described is dependent upon the chemical stability of the olive oil reference sample. Excessive heating or abuse can cause oxidation resulting in the formulation of solids and lower pulsed NMR readings. The Committee recommends replacement of the reference sample oil every three months with fresh olive oil which has been kept under refrigeration. While it is not the Committee's place or intent to recommend a specific oil, it is noted that the collaborative study was conducted using a high grade Lucca Olive Oil from Italy.
3. Push retest button one time before making NMR reading on first sample tested in each probe, as recommended by the Instrument Manufacturer.
4. The basic procedure described is applicable to unhydrogenated palm oils and blends containing unhydrogenated palm oils. The Committee recognized that other palm oil type samples and/or blends do produce poor reproducibility and further work is planned in this direction to establish tempering conditions prior to measurement.
5. These values of reproducibility are an indication of the precision obtainable by this method of measurement when polymorphic stability of the sample is not a factor. The tristearin in olive oil mixtures are also used as reference samples for the calibration of the instrument. These mixtures are melted and liquid readings taken at 70° C. before being tempered and measured by this method. The Solid Fat Content (SFC) values measured agree well with the percentage of solids by weight. A single fifth order polynomial regression equation is recommended for solids contents of 95% or less. Polynomial coefficients, correlation coefficients and interpolation tables for conversion of calculated solids to calibration corrected solids can be obtained from the manufacturer for each instrument.

The calibration procedure is also provided by the manufacturer.

4. Complete Melting Point of Polyol Polyesters by Differential Scanning Calorimetry (DSC)

The complete melting point of the polyol polyester material or polyol polyester-containing particles used in this invention can be determined by DSC as follows:

Equipment:
Perkin-Elmer 7 Series Thermal Analysis System, Model DSC7, manufactured by Perkin-Elmer, Norwalk, Conn.
Procedure:

1. Sample of polyol polyester material or polyol polyester-containing particles is heated to at least 10° C. above the temperature at which all visible solids are melted and mixed thoroughly.
2. 10±2 mg of sample is weighed into sample pan.
3. A scan is performed from about 10° C. above the temperature at which all visible solids are melted to −60° C. at 5° C. per minute.
4. The temperature of the sample is maintained at −60° C. for 3 minutes and scanned from −60° C. to the original starting temperature at 5° C. per minute (i.e., to about 10° C. above the temperature at which all visible solids are melted).
5. The complete melt point is the temperature at the intersection of the base line (i.e. specific heat line) with the line tangent to the trailing edge of the endothermic peak.

5. Thickness of Solid Polyol Polyester Particle (Light Microscopy)

The thickness of the solid polyol polyester particles formed in the nondigestible fat compositions herein may be estimated at room temperature with a Nikon Microphot video-enhanced light microscope (VELM) using Hoffman Modulation Contrast (HMC) optics according to the following method:

1. A small portion (i.e., 1–10 mg) of the nondigestible fat sample with the solid polyol polyester particles dispersed therein is placed on a microscope slide and covered. The slide is placed under the microscope.
2. The sample is examined using a HMC 100X oil objective as the standard lens in conjunction with a 10X eyepiece lens.
3. A microscope-mounted video camera and associated controller are used for video enhancement to facilitate differentiation between the sample and the background.
4. The thickness of the solid polyol-polyester particles is measured in um.

This method permits differentiation of particles having thicknesses just within the resolution of the VELM (approximately 0.2–0.5 um). Particle thickness of particles having smaller dimensions can be determined by the Freeze Fracture Method described hereinafter.

(Note: No special sample preparation is required, other than obtaining a representative sample. The samples should be melted and cooled ambiently.)

Reference: Robert Hoffman, "The Modulation Contrast Microscope: Principles and Performances", *Journal of Microscopy*, Vol. 110, Pt 3, August 1977, pp. 205–222.

6. Thickness of Solid Polyol Polyester Particle (Freeze Fracture Transmission Electron Microscopy)

The three-dimensional topography of particles and their size can be determined by a freeze-fracture transmission electron microscopy (ff-tem) method.

This freeze-fracture method is carried out as follows:
1. The outside cavity of a freezing container is filled with liquid $N_2$ and the inner dewar of the freezing container is filled with liquid ethane (normal melting temperature of −172° C.). The ethane is allowed to freeze.
2. A small amount (1–2 ul) of the nondigestible fat sample with the polyol polyester particles dispersed therein is placed in the well of a gold-plated Balzers specimen holder. (Note: for very fluid samples, 1–2 ul of sample is placed on a gold planchet (Baizers) and another planchet is placed on top of the first to form a sandwich.)
3. Most of the frozen ethane in the dewar is melted by inserting a metal heat sink (e.g., tweezers) into the dewar.
4. Immediately after melting the ethane, the specimen holder containing the nondigestible fat sample is picked up using a pair of tweezers and rapidly plunged into the liquid ethane.
5. After a few seconds, the specimen holder is removed from the ethane, quickly touched to the tip of a camel's hair brush to remove excess ethane, and immediately immersed in the liquid $N_2$ to keep the sample cold.
6. The sample is transferred under liquid $N_2$ to a JEOL JFD-9000C sample holder and then transferred into the chamber of a JEOL JFD-9000C freeze-fracture unit. The temperature of the unit should be about −175° C. Vacuum should be at least $8 \times 10^{-7}$ torr.
7. A knife is cooled to a temperature of about −165° C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500V and the current is 70 mA.
10. The samples are removed from the freeze fracture unit and cleaned using 3 washes of chloroform.
11. The replica is picked up on a 300 mesh copper EM grid and examined in a transmission electron microscope.
12. Images are recorded on negative film and positive prints are made from the negatives.
13. The thickness of the polyol polyester particles is measured in nm.

References:
Rash, J. E. and Hudson, C. S., *Freeze Fracture: Methods, Artifacts, and Interpretations,* New Haven Press, New York, 1979.

Stolinski and Breathnach, *Freeze Fracture Replication of Biological Tissues,* Academic Press, London, 1975.

Steinbrecht and Zierold, *Cryotechniques in Biological Electron Microscopy,* Springer-Verlag, Berlin, 1987.

H. Specific Examples

Preparation of the nondigestible fat compositions of the present invention is illustrated by the following examples:

EXAMPLE I

Solid Sucrose Polyester Preparation

Behenic Methyl Ester Preparation

Behenic methyl esters are prepared from about 870 grams of o hydrogenated high erucic rapeseed oil, about 174 grams of methanol, and about 12.2 grams of sodium methoxide solution (25% in methanol) are added to a spherical 3-liter glass reactor. The reactor has a heating mantle, thermometer, temperature controller, reflux condenser, variable speed agitator, vacuum take-off, and bottom outlet. The mixture is reacted at about 65° C. for approximately 1.5 hours, while refluxing the methanol. The agitation is stopped, and the glycerin by-product from the rapeseed oil is allowed to settle for about 30 minutes. The glycerin settles to the bottom of the reactor, and is removed through the bottom outlet. About 30 additional grams of methanol, and about 5.2 grams of sodium methoxide solution (25% in methanol) are added to the glass reactor, and the mixture is reacted at about 65° C. for about 30 minutes. The agitation is stopped, the glycerin is allowed to settle for about 30 minutes, and is removed through the bottom outlet. About 100 grams of water are added to the mixture, stirred allowed to settle, and removed through the bottom outlet. The water-washing procedure is repeated two more times. The reflux condenser is removed, and vacuum is applied to the reactor, and the residual water and methanol are evaporated. The vacuum is broken, and a fractionation column is added to the reactor. The reactor is heated to about 170°–200° C. under a vacuum of about 0.3–1.0 mm Hg. Approximately 50% of the first material to evaporate from the column is collected and discarded. The next 40% (approximately) of the material to evaporate from the column is collected as product. This product is approximately 92% by weight methyl behenate.

Sucrose Esterification

About 21.2 grams of methyl o-toluate (Aldrich Chemical Company) are mixed with about 366.2 grams of the behenic methyl esters. The molar ratio of toluic to behenic is about 1:7. About 152.6 grams of this methyl ester mixture are mixed in a 1-liter glass reactor along with about 34.4 grams of powdered sucrose, about 24 grams of powdered potassium stearate and about 1.4 grams of powdered potassium carbonate. The reactor has a heating mantle, thermometer, temperature controller, variable speed agitator, vacuum take-off, and bottom outlet. The mixture is agitated and heated at about 135° C. at about 15 mm Hg vacuum for about 1.5 hours. After about 1.5 hours, the vacuum is broken with nitrogen, and the remaining 234.8 grams (approximately) of the methyl ester mixture, along with about 1.4 grams of potassium carbonate are added to the reaction mixture. This mixture is reacted at about 135° C. under about 0.5–5.8 mm Hg for about 5 hours. The mixture is cooled to about 75° C., and about 30 grams of water are added to the mixture. The mixture is transferred to jars and centrifuged (Fischer Scientific Model Marathon 10K Centrifuge) at about 2500 RPM for about 2 minutes. The liquid in the jars is then decanted from the soap layer at the bottom of the jars. About 5 grams of silica are added to the decanted liquid, and the mixture is stirred for about 30 minutes at about 75° C. The mixture is then filtered through filter paper using a Buchner funnel. The filtrate is then fed through a Pope 2-inch diameter wiped film evaporator at approximately 30 grams/hour to distill the unreacted methyl esters. The evaporator operates at about 235° C. under about 0.05–0.08 mm Hg. The product is then collected from the evaporator and cooled to ambient temperature.

This solid sucrose polyester product has a complete melting point of 70.5° C. (as measured by DSC described in the Analytical Methods section hereinafter) and is 99.0% esterified.

Preparation of Fat Composition

Six grams of this solid sucrose polyester product and 94 grams of a liquid sucrose polyester, in which the sucrose is substantially completely esterified with fatty acid groups of cottonseed oil, are mixed and heated until all the solids are dissolved. The mixture is then allowed to cool back to room temperature at a rate of 33.3° F./minute. The cooling brings about crystallization of the solid sucrose polyester material in the form of small, platelet-like particles which are dispersed in the liquid nondigestible oil. FIGURE 1 is a photomicrograph depicting the two dimensional, platelet-like structure of the solid polyol polyester particles. These platelet-like particles have a thickness of less than about 100 nm as measured by Freeze Fracture Transmission Electron Microscopy described hereinbefore in the Analytical Methods section.

The fat composition comprising the sol id particles of sucrose polyester dispersed in the liquid sucrose polyester has an SFC profile slope of −0.1% solids/°F. The composition is suitable for use as a food fat, and does not produce passive oil loss which would otherwise result if only liquid sucrose polyester is used as a food fat. Also, since the level of solids in these fat compositions is so low, food products containing these fat compositions will not be waxy tasting.

The above solid sucrose polyester and liquid sucrose polyester have the attributes shown in Table I:

TABLE I

|  | SOLID SUCROSE POLYESTER % | LIQUID SUCROSE POLYESTER % |
|---|---|---|
| FATTY ACID CONTENT | | |
| $C_{14}$ | — | 0.5 |
| $C_{16}$ | 0.1 | 20.3 |
| $C_{18}$ | 2.0 | 6.2 |
| $C_{18:1}$ | — | 37.3 |
| $C_{18:2}$ | 0.2 | 34.2 |
| $C_{18:3}$ | — | 0.3 |
| $C_{20}$ | 7.8 | 0.3 |
| $C_{22}$ | 88.4 | — |
| $C_{24}$ | 0.1 | — |
| Toluic | 1.4 | — |
| Other | — | 0.9 |
| ESTER DISTRIBUTION | | |
| Octa | 92.9 | 74.6 |
| Hepta | 6.7 | 25.0 |
| Hexa | 0.4 | <0.1 |
| Lower | — | <0.1 |

EXAMPLE II

Solid Sucrose Polyester Preparation

About 15.0 grams of methyl 3-methylbenzoate (Aldrich Chemical Company) are mixed with about 345.2 grams of behenic methyl esters described in example 1. About 150.00 grams of this methyl ester mixture are mixed in a 1-liter glass reactor along with 28.5 grams of powdered sucrose, about 20 grams of powdered potassium stearate and about 1.2 grams of powdered potassium carbonate. The reaction is then run similarly to the reaction described in Example I.

The solid sucrose polyester product has a complete melting point of 73.4° C. and is 99.2% esterified.

Fat Composition Preparation

Four grams of this solid sucrose polyester product and 96 grams of the liquid sucrose polyester described in Example I are mixed and heated until all the solids are dissolved. The mixture is allowed to cool back to room temperature. The resulting fat composition has an SFC profile slope of −0.1 and is suitable for use as a food fat. It does not produce passive oil loss which would result if the liquid sucrose polyester were used alone. Also, since the level of solids in these fat compositions is so low, food products containing these fat compositions will not be waxy tasting.

The above solid sucrose polyester has the attributes shown in Table II.

TABLE II

|  | SOLID SUCROSE POLYESTER % |
|---|---|
| FATTY ACID COMPOSITION | |
| $C_{14}$ | — |
| $C_{16}$ | 0.1 |
| $C_{18:0}$ | 1.9 |
| $C_{18:1}$ | — |
| $C_{18:2}$ | 0.2 |
| $C_{18:3}$ | — |

TABLE II-continued

| | SOLID SUCROSE POLYESTER % |
|---|---|
| $C_{20}$ | 7.7 |
| $C_{22}$ | 88.8 |
| $C_{24}$ | 0.1 |
| Methyl Benzoic | 1.1 |
| Other | 0.1 |
| Ester Distribution | |
| Octa | 94.2 |
| Hepta | 5.3 |
| Hexs | 0.5 |
| Lower | 0.0 |

EXAMPLE III

Solid Sucrose Polyester Preparation

About 8 grams of methyl tricontanoate (Sigma Chemical Company) are mixed with about 42.0 grams of behenic methyl esters described in example 1. About 25 grams of this methyl ester mixture are mixed in a 100-ml glass reactor along with 4.7 grams of powdered sucrose, about 2.3 grams of potassium stearate, and about 0.3 grams of powdered potassium carbonate. The reaction is then run similarly to the reaction described in Example I.

The solid sucrose polyester product comprises about 68.7% octaester.

Fat Composition Preparation

This solid sucrose polyester may be blended with the liquid nondigestible oil described in Example I at levels as low as 2% to form a nondigestible fat composition suitable for use as a food fat, which composition does not produce passive oil loss which would result if the liquid nondigestible oil were used alone.

EXAMPLE IV

Norchip potatoes are used which have been sliced to a thickness of about 0.052 inches (0.13 cm). The sliced potatoes are fried in a 5 pound batch fryer at a temperature of 365° F. (185° C.) for 3 minutes. Approximately 225 potato chips are fried in each of the the fat compositions of Examples I, II, and III.

Ingestion of these potato chips which contain the nondigestible fat compositions will not result in passive oil loss, and the potato chips are not unacceptably waxy tasting.

What is claimed is:

1. A nondigestible fat composition useful as a replacement for triglyceride fats or oils in foods, which composition has a Solid Fat Content profile slope between 70° F. and 98.6° F. of from 0 to about −0.75 % solids/°F. and which composition comprises:
   A. a liquid nondigestible oil having a complete melting point below about 37° C.; and
   B. nondigestible solid particles of polyol polyester material dispersed in said oil in an amount sufficient to control passive oil loss upon ingestion of said composition, said nondigestible solid particles having a complete melting point above about 37° C. and a thickness of about 1 micron or less, wherein the ester groups forming said polyol polyester material consist essentially of
      (i) at least about 15% ester groups formed from $C_{20}$–$C_{26}$ long chain saturated fatty acid radicals, and
      (ii) other ester groups formed from fatty or other organic acid radicals which are dissimilar to said long chain saturated fatty acid radicals;
   the molar ratio of said dissimilar radicals to said long chain saturated fatty add radicals ranging from about 0.1:7.9 to about 3:5, provided further that said dissimilar radicals not consist solely of $C_2$–$C_{12}$ short chain saturated fatty acid radicals, $C_{12}$ or higher long chain unsaturated fatty acid radicals, or a combination of said short chain saturated or said long chain unsaturated fatty acid radicals.

2. The nondigestible fat composition of claim 1 which comprises from about 60% to about 99% liquid nondigestible oil and from about 1% to about 40% solid polyol polyester particles.

3. The nondigestible fat composition of claim 2 wherein in the polyol polyester material forming the solid particles the molar ratio of dissimilar acid radicals to long chain saturated fatty acid radicals ranges from about 0.5:7.5 to about 2:6.

4. The nondigestible fat composition of claim 3 wherein in the nondigestible particles the solid polyol polyester material contains at least about 30% of said long chain saturated fatty acid radicals.

5. The nondigestible fat composition of claim 4 wherein in the nondigestible particles the polyol moiety of the solid polyol polyester material is derived from a sugar or sugar alcohol having from 6 to 8 hydroxy groups and wherein said particles have a thickness of 0.1 micron or less.

6. The nondigestible fat composition of claim 5 wherein the liquid nondigestible oil is a liquid sucrose fatty acid polyester.

7. The nondigestible fat composition of claim 6 wherein in the nondigestible particles the polyol moiety of the solid polyol polyester material is derived from sucrose and wherein said solid polyol polyester material contains at least about 50% long chain saturated fatty acid radicals.

8. The nondigestible fat composition of claim 7 having a Solid Fat Content profile slope between 70° F. and 98.6° F. of from 0 to about −0.5 % solids/°F.

9. The nondigestible fat composition of claim 8 wherein in the polyol polyester material forming the nondigestible particles the long chain saturated fatty acid radicals consist essentially of behenic acid radicals.

10. The nondigestible fat composition of claim 9 wherein in the polyol polyester material forming the nondigestible particles the dissimilar acid radicals are selected from benzoic, toluic, aminobenzoic, aminomethylbenzoic, hydroxybenzoic, vanillic, salicylic, anisic, acetylmandelic, chlorobenzoic, dichlorobenzoic, bromobenzoic, fluorobenzoic, acetylbenzoic, cumic, phenylbenzoic, nicotinic, fluorene carboxlylic, indole carboxylic, methyl stearic, isobutyric, isovaleric, tricontanoic, tricontenoic, cyclobutane carboxylic, cyclopentane carboxylic, lo cyclohexane carboxylic, cyclohexane acetic, ascorbic, abietic, polyacrylic, dimer fatty acid, chlorostearic, chlorocaprylic, chloracetic, bromostearic, bromocaprylic, bromoacetic, aminocaprylic, aminostearic, benzoylbutyric, and phenylacetic radicals.

11. The nondigestible fat composition of claim 10 which comprises from about 80% to 99% liquid nondigestible oil and from about 1% to about 20% of the solid polyol polyester particles.

12. A nondigestible fat composition useful as a replacement for triglyceride fats or oils in foods, which composition has a Solid Fat Content profile slope between 70° F. and 98.6° F. of from 0 to about −0.3% solids/°F. and which composition comprises:

A. from about 85% to about 99% liquid sucrose fatty acid polyester; and

B. from about 1% to about 15% particles of solid sucrose fatty acid polyester material, said particles having a complete melting point above about 37° C. and a thickness of about 1 micron or less, wherein the ester groups forming said polyester material consist essentially of
   (i) at least about 80% ester groups formed from $C_{20}$–$C_{26}$ long chain saturated fatty acid radicals, and
   (ii) other ester groups formed from fatty or other organic acid radicals which are dissimilar to said long chain saturated fatty acid radicals;
   the molar ratio of said dissimilar acid radicals to said long chain saturated fatty acid radicals ranging from about 1:7 to about 1.5:6.5; provided further that said dissimilar radicals not consist solely of $C_2$–$C_{12}$ short chain saturated fatty acid radicals, $C_{12}$ or higher long chain unsaturated fatty acid radicals, or a combination of said short chain saturated or said long chain unsaturated fatty acid radicals.

13. The nondigestible fat composition of claim 12 wherein the solid particles have a thickness of less than 0.1 micron.

14. The nondigestible fat composition of claim 13 having a Solid Fat Content profile slope between 70° F. and 98.6° F. of from 0 to about –0.1% solids/°F.

15. The nondigestible fat composition of claim 14 wherein the nondigestible solid particles have a complete melting point above about 50° C.

16. A nondigestible fat composition useful as a replacement for triglyceride fats or oils in foods, which composition has a Solid Fat Content profile slope between 70° F. and 98.6° C. of from 0 to about –0.75% solids/°F. and which composition comprises:

A. a liquid nondigestible oil having a complete melting point below about 37° C.; and B. nondigestible solid particles of polyol polyester material dispersed in said oil in an amount sufficient to control passive oil loss upon ingestion of said composition, said nondigestible solid particles having a complete melting point above about 37° C. and a thickness of less than about 1 micron, wherein the ester groups forming said polyol polyester material consist essentially of
   (i) at least about 15% ester groups formed from $C_{20}$–$C_{26}$ long chain saturated fatty acid radicals, and
   (ii) other ester groups formed from fatty or other organic acid radicals which are dissimilar to said long chain saturated fatty acid radicals, wherein the dissimilar acid radicals are selected from aromatic substituted or unsubstituted acid radicals, ultra-long chain saturated or unsaturated acid radicals, branched cyclic substituted or unsubstituted acid radicals, polymeric ester-forming radicals or alkyl chain radicals with functional groups attached thereto;
   the molar ratio of said dissimilar radicals to said long chain saturated fatty acid radicals ranging from about 0.1:7.9 to about 3:5.

17. A food product comprising an edible substrate and from 10% to 100% of the nondigestible fat composition of claim 1.

18. The food product of claim 16 wherein the edible substrate is a potato chip.

19. A thickened digestible oil product comprising:

A. from about 85% to about 99% of a digestible edible oil; and

B. from about 1% to about 15% particles of solid sucrose fatty acid polyester material, said particles having a complete melting point above about 37° C. and a thickness of less than about 1 micron, wherein the ester groups forming said polyol polyester material consist essentially of
   (i) at least about 15% ester groups formed from $C_{20}$–$C_{26}$ long chain saturated fatty acid radicals, and
   (ii) other ester groups formed from fatty or other organic acid radicals which are dissimilar to said long chain saturated fatty acid radicals; the molar ratio of said dissimilar acid radicals to said long chain saturated fatty acids ranging from about 0.1:7.9 to about 3:5, provided further that said dissimilar radicals not consist solely of $C_2$–$C_{12}$ short chain saturated fatty acid radicals, $C_{12}$ or higher long chain unsaturated fatty acid radicals, or a combination of said short chain saturated and said long chain unsaturated fatty acid radicals.

* * * * *